United States Patent
Lin et al.

(10) Patent No.: US 6,458,180 B1
(45) Date of Patent: Oct. 1, 2002

(54) AMALGAMATABLE DENTAL ALLOY POWDER HAVING AN EFFECT OF REDUCING INITIAL MERCURY VAPOR RELEASE RATE

(75) Inventors: Jiin-Huey Chern Lin, 911 Tower Rd., Winnetka, IL (US) 60093; Chien-Ping Ju, 91 Pineview Rd., Carbondale, IL (US) 62901; Chao-Chin Ning; Hsuan-I Huang, both of Kaohsiung (TW)

(73) Assignees: Jiin-Huey Chern Lin, Winnetka, IL (US); Chien-Ping Ju, Carbondale, IL (US)

( * ) Notice: Subject to any disclaimer, the term of this patent is extended or adjusted under 35 U.S.C. 154(b) by 0 days.

(21) Appl. No.: 09/756,768

(22) Filed: Jan. 10, 2001

(51) Int. Cl.$^7$ .................................................. B22F 1/00
(52) U.S. Cl. ....................................................... 75/255
(58) Field of Search .......................... 75/255; 148/513, 148/430

(56) References Cited

U.S. PATENT DOCUMENTS

| | | | | |
|---|---|---|---|---|
| 3,871,876 A | * | 3/1975 | Asgar et al. ................. | 148/400 |
| 3,933,961 A | * | 1/1976 | Burns ........................... | 419/63 |
| 4,235,631 A | * | 11/1980 | Aliotta et al. | |
| 4,264,354 A | * | 4/1981 | Cheetham ..................... | 75/342 |
| 4,374,085 A | * | 2/1983 | Asgar et al. ................. | 420/470 |
| 4,479,823 A | * | 10/1984 | Hohmann | |
| 4,664,629 A | * | 5/1987 | Chodkowski ............ | 433/228.1 |
| 4,664,855 A | * | 5/1987 | Tremblay et al. .............. | 264/11 |
| 4,859,240 A | * | 8/1989 | Parker | |
| 4,859,412 A | * | 8/1989 | Groll et al. .................... | 419/23 |
| 5,185,125 A | * | 2/1993 | Smith et al. ................. | 420/503 |

OTHER PUBLICATIONS

K.I. Chen, C.P. Ju and J.H. Chern Lin, "Effect of Particle Configuration On Structure and Properties of Dispersed PD–Containing Dental Amalgam", Biomaterials 20 (199) 1851–1866.

J.H. Chern Lin, H.C. Lee and C.P. Ju, "Effect Of Addition of Palladium on Properties of Ag2Hg3 ($Y_1$)Phase" Biomaterials 18 (1997) 939–946.

* cited by examiner

Primary Examiner—Ngoclan Mai
(74) Attorney, Agent, or Firm—Bacon & Thomas

(57) ABSTRACT

The present invention provides an amalgamatable dental alloy powder for making an amalgam having a low initial mercury vapor release rate having a composition comprising 50–80 wt % Ag; 10–30 wt % Cu, and 10–35 wt % Sn, and optionally less than 7 wt % of Pd, which is prepared by subjecting a single-alloy powder having a particle size ranging from 1 to 55 microns with a majority thereof having a particle size less than 20 microns to a heat treatment, or separately subjecting a Ag—Cu—Sn powder having a particle size ranging from 1 to 70 microns with a majority thereof having a particle size less than 30 microns and a Ag—Cu—Pd powder having a particle size ranging from 1 to 100 microns with a majority thereof having a particle size less than 45 microns to heat treatments, and subjecting the heat treated powders to a pickling treatment.

22 Claims, No Drawings

AMALGAMATABLE DENTAL ALLOY POWDER HAVING AN EFFECT OF REDUCING INITIAL MERCURY VAPOR RELEASE RATE

FIELD OF THE INVENTION

The present invention is related to a dental amalgam, and in particular to an amalgamatable dental alloy powder for making an amalgam having a low initial mercury vapor release rate.

BACKGROUND OF THE INVENTION

Amalgamatable dental alloys are typically silver based alloys in particulate form which can be mixed with mercury to produce an amalgam which is initially soft and pliable but which sets to a hard mass after a time. Thus, when fresh amalgam is placed in a tooth cavity it can be worked by the dentist to completely fill the cavity and to have an external configuration consistent with that of the remainder of the tooth.

It was known that an amalgamgtable alloy powder can be prepared from an all-in-one alloy having a desired composition or can be formed by mixing an amalgamatable silver-base alloy matrix powder and a non-amalgamatable alloy dispersant powder in a controlled ratio to meet the desired composition. Such alloy powders can be in the form of irregularly-shaped microgranules, flakes or filings, made by mechanical refining; or in the form of spherical particles derived from a microcasting of a molten mass of the alloy, such as by fluid atomization techniques or the like.

Two of the present inventors and their co-worker have studied the effect of particle configuration on the structure and properties of four dispersed types of Pd-containing amalgam alloy powder admixtures with the same composition, including a blend of spherical (atomized) matrix particles with spherical dispersant particles; a blend of spherical matrix particles with irregular (lathe-cut) dispersant particles; a blend of irregular matrix particles with spherical dispersant particles; and a blend of irregular matrix particles with irregular dispersant particles [K. I. Chen, C. P. Ju, and J. H. Chern Lin, entitled "Effect of particle configuration on structure and properties of dispersed Pd-containing dental amalgam", Biomaterials 20 (1999) 1851–1866]. One of the properties investigated therein was an early stage mercury vapor release rate of amalgam, and the investigation showed that the early stage mercury vapor release rate of the amalgams comprising irregular dispersant particles were significantly lower than those of amalgams comprising spherical dispersant particles.

It is clearly that there is still a great interest in further reducing the early stage release rate of mercury vapor from the dental amalgam, which constitutes the major portion of the mercury vapor released from the dental amalgam during its preparation and when it is worn in vivo.

SUMMARY OF THE INVENTION

The present invention provides an amalgamatable dental alloy powder for making an amalgam having a low initial mercury vapor release rate having a composition comprising 50–80 wt % Ag; 10–30 wt % Cu, and 10–35 wt % Sn, and optionally less than 7 wt % of Pd, and having a particle size ranging from 1 to 100 microns with a majority thereof having a particle size less than 45 microns, which is prepared by a process comprising the following steps i) and ii), or steps I) and II):

i) subjecting a single-alloy powder having a particle size ranging from 1 to 55 microns with a majority thereof having a particle size less than 20 microns to a first heat treatment;

ii) subjecting the heat treated single-alloy powder to a pickling treatment;

I) subjecting a Ag—Cu—Sn powder having a particle size ranging from 1 to 70 microns with a majority thereof having a particle size less than 30 microns to a second heat treatment, and subjecting a Ag—Cu—Pd powder having a particle size ranging from 1 to 100 microns with a majority thereof having a particle size less than 45 microns to a third heat treatment;

II) subjecting the heat treated Ag—Cu—Sn powder and the heat treated Ag—Cu—Pd powder to a pickling treatment;

wherein said heat treatments comprise heating said powder at a temperature ranging from 100 to 600° C. in an inert atmosphere for a period ranging from 0.5 hours to 8 days, preferably from 100 to 500° C. and for a period ranging from 24 hours to 48 hours provided that said powder maintain a powder form or a loose agglomerate form after said heat treatment, whereby an amalgam made from said amalgamatable dental alloy powder has a reduced initial mercury vapor release rate.

The inventors of the present application also surprisingly found that the amalgamatable dental alloy powder of the present invention prepared from said single-alloy powder can have a significantly lower content of Sn, i.e. lower than 20 wt %, without jeopardizing the performance of the amalgams.

Preferably, the amalgamatable dental alloy powder of the present invention is free from Pd and is prepared by the process comprising steps i) and ii). Preferably, said composition of said amalgamatable dental alloy powder comprises 60–70 wt % Ag; 10–20 wt % Cu, and 10–30 wt % Sn, and more preferably 60 wt % Ag, 13 wt % Cu and 27 wt % Sn.

Alternatively, the amalgamatable dental alloy powder of the present invention comprises Pd and is prepared by the process comprising steps i) and ii). Preferably, said composition of said amalgamatable dental alloy powder comprises 10–20 wt % Sn, and more preferably comprises 60–70 wt % Ag; 10–20 wt % Cu, and 2–4 wt % Pd.

Preferably, said first heat treatment comprises heating said single-alloy powder at a temperature ranging 300 to 500° C. and for a period ranging from 24 hours to 48 hours.

Preferably, the amalgamatable dental alloy powder of the present invention is prepared by the process comprising steps I) and II).

Preferably, said Ag—Cu—Sn powder with a majority thereof have a particle size less than 20 microns and said Ag—Cu—Pd powder with a majority thereof have a particle size less than 35 microns. More preferably, said Ag—Cu—Sn powder with a majority thereof have a particle size less than 10 microns and said Ag—Cu—Pd powder with a majority thereof have a particle size less than 25 microns.

Preferably, said heat treated Ag—Cu—Sn powder and said heat treated Ag—Cu—Pd powder are separately subjected to said pickling treatment.

Preferably, said second heat treatment comprises heating said Ag—Cu—Sn powder at a temperature ranging from 300 to 500° C. for a period ranging from 24 hours to 48 hours, and said third heat treatment comprises heating Ag—Cu—Pd powder at a temperature ranging from 100 to 500° C. for a period ranging from 24 hours to 48 hours. More preferably, said second heat treatment comprises heating said Ag—Cu—Sn powder at 400° C. for 24 hours, and said third heat treatment comprises heating Ag—Cu—Pd powder at a temperature ranging from 100 to 400° C. for 48 hours.

When the amalgamatable dental alloy powder of the present invention is prepared by the process comprising steps I) and II), the composition thereof preferably comprises 60–70 wt % Ag; 10–20 wt % Cu, 10–30 wt % Sn and 2–4 wt % Pd, and more preferably 67.2 wt % Ag, 12.0 wt % Cu, 17.4 wt % Sn, and 3.4 wt % Pd.

Preferably, said Ag—Cu—Sn powder comprise 70 wt % Ag, 4 wt % Cu and 26 wt % Sn, and said Ag—Cu—Pd powder comprise 62 wt % Ag, 28 wt % Cu and 10 wt % Pd.

DETAILED DESCRIPTION OF THE PREFERRED EMBODIMENTS

In the preferred embodiments of the present invention, two different types of amalgamatable dental alloy powders were made and used in the preparation of amalgams, which include a single-alloy powder, and a mixed powder of a matrix alloy and a dispersant alloy. Further, a commercially available amalgamatable single-alloy powder was directly used. As shown by the following examples, the amalgamatable dental alloy powders prepared according to the present invention have significantly lower early stage mercury vapor release rates and comparable mechanical properties in comparison with the commercial amalgam dental alloy powders.

EXAMPLES 1–6

Single-alloy Powder

Spherical particles of a four-component alloy having a composition of 68.7 wt % Ag, 13.3 wt % Cu, 14.7 wt % Sn and 3.3 wt % Pd were formed by melting particles of the four pure metals in an inert atmosphere to a homogenous fluid and atomizing the fluid into an inert atmosphere with a high pressure. The atomized spherical particles had a particle size ranging from several microns to less than 100 microns with a majority thereof having a particle size less than 20 microns.

The atomized spherical particles so prepared together with a commercially available single-alloy powder Tytin® having a composition of 60 wt % Ag, 27 wt % Sn and 13 wt % Cu were subjected to heat treatments of different conditions listed in Table 1, wherein the powder was encapsulated in a quartz tube having an argon pressure of about 30 mm-Hg prior to the heat treatment.

TABLE 1

| | | |
|---|---|---|
| Ex. 1 | No heat treatment | 68.7 wt % Ag, 13.3 wt % Cu, 14.7 wt % Sn, 3.3 wt % Pd |
| Ex. 2 | 400° C., 24 hr | 68.7 wt % Ag, 13.3 wt % Cu, 14.7 wt % Sn, 3.3 wt % Pd |
| Ex. 3 | 400° C., 48 hr | 68.7 wt % Ag, 13.3 wt % Cu, 14.7 wt % Sn, 3.3 wt % Pd |
| Ex. 4 | 400° C., 96 hr | 68.7 wt % Ag, 13.3 wt % Cu, 14.7 wt % Sn, 3.3 wt % Pd |
| Ex. 5 | No heat treatment | 60 wt % Ag, 27 wt % Sn and 13 wt % Cu |
| Ex. 6 | 400° C., 24 hr | 60 wt % Ag, 27 wt % Sn and 13 wt % Cu |

The alloy powders after the heat treatments were examined by SEM, and found that the majority thereof remained in the particulate form with some loose agglomerates which were broken after shaking by hand.

The heat treated alloy powders were subject to a pickling treatment comprising sinking the powders in 10 wt % HCl aqueous solution in a ratio of 10 ml acidic solution per gram of powder, supersonicating the mixture 30 minutes, washing with deionized water three times, and drying at 50–70° C. for 12 hours.

EXAMPLES 7 and 8

Mixed Powder

The matrix alloy (70 wt % Ag-4 wt % Cu-26 wt % Sn) and dispersant alloy (62 wt % Ag-28 wt % Cu-10 wt % Pd) were prepared from raw materials of 99.99% pure silver, 99.99% pure copper, 99.5% pure palladium and 99.9% pure tin. Particles were prepared by first melting the desired metals in a quartz tube sealed in argon gas. After 30 min at 1150° C., the molten alloys were furnace cooled to room temperature. The Ag—Cu—Pd ingots were homogenized at 600° C., while the Ag—Cu—Sn ingots were homogenized at 400° C. for 24 hours.

The homogenized ingots were then mounted in a lathe and comminuted with steel files. The lathe-cut irregular particles were collected and ball-milled for different periods of time, and the particle distributions thereof were analyzed. The results are shown in Table 2A and Table 2B.

TABLE 2A

Particle distribution of Ag—Cu—Sn

| Diameter | Volume percentages Ball-milling time (min) | | | | | | |
|---|---|---|---|---|---|---|---|
| (μm) | 0 | 10 | 15 | 20 | 25 | 30 | 35 |
| 0–10 | 0.5 | 44 | 37.5 | 37.5 | 31 | 58.5 | 40 |
| 10–20 | 5.5 | 7 | 41 | 36 | 41 | 32 | 39 |
| 20–30 | 14 | 13.5 | 14.5 | 16 | 19.5 | 8 | 14.5 |
| 30–40 | 35 | 3 | 2.5 | 7.5 | 4 | 1 | 3 |
| 40–50 | 31 | 1.5 | 1.5 | 2 | 2 | 0.5 | 1.5 |
| 50–60 | 9 | 0.5 | 1.5 | 1 | 1.5 | | 1 |
| 60–70 | 4 | 0.5 | 1.5 | | 1 | | 1 |
| 70–80 | 1 | | | | | | |

TABLE 2B

Particle distribution of Ag—Cu—Pd

| Diameter | Volume percentages Ball-milling time (min) | | | | | | |
|---|---|---|---|---|---|---|---|
| (μm) | 0 | 15 | 25 | 35 | 45 | 55 | 65 |
| 0–10 | 0.5 | 6 | 2.5 | 11 | 13 | 15 | 14 |
| 10–20 | 3.5 | 7.5 | 6 | 11 | 15 | 23 | 21 |
| 20–30 | 12 | 17 | 11 | 16.5 | 16.5 | 22 | 25 |
| 30–40 | 24 | 19 | 14 | 18 | 29.5 | 15 | 17.5 |
| 40–50 | 37 | 18 | 18 | 15 | 15.5 | 11 | 12 |
| 50–60 | 15 | 14 | 16 | 9 | 11 | 7 | 7 |
| 60–70 | 7 | 9.5 | 11 | 7 | 4 | 4 | 2 |
| 70–80 | 1 | 4.5 | 12 | 6 | 3 | 1.5 | 1.5 |
| 80–90 | | 4 | 5 | 4 | 2.5 | 1 | |
| 90–100 | | | 4 | 2 | | 0.5 | |
| 100–120 | 0.5 | 0.5 | 0.5 | | | | |

The Ag—Cu—Sn lathe-cut particles with 10-minute ball-milling and the Ag—Cu—Pd lathe-cut particles with 65-minute ball-millings were sieved through a #325 mesh to obtain particles with sizes less than 45 microns. The sieved particles were subjected to the heat treatment and pickling treatments according to the conditions listed in Table 3.

TABLE 3

| | Heat treatment temperature and time | | Pickling time, |
|---|---|---|---|
| | 70% Ag—4% Cu—26% Sn | 62% Ag—28% Cu—10% Pd | min. |
| Ex. 7 | 100° C., 48 hr | 100° C., 48 hr | 10 |
| Ex. 8 | 400° C., 24 hr | 100° C., 48 hr | 30 |
| Ex. 9 | 400° C., 24 hr | 200° C., 48 hr | 30 |
| Ex. 10 | 400° C., 24 hr | 400° C., 48 hr | 30 |

Trituration of the alloy powder and mercury were carried out in a closed capsule using a commercial mechanical triturator (Crescent LP-60, Lyons, Ill., USA). The mercury/alloy ratios for Ex. 1 to Ex. 10 alloys are listed in Table 4. After trituration, the amalgam mass was hand-condensed in a disk-shaped acrylic die of 1 cm in diameter and 2mm in thickness for the mercury vapor release measurement, and a die of 4 mm in diameter and 8 mm in height for the compressive strength and creep tesets.

TABLE 4

| | mercury/alloy ratio |
|---|---|
| Ex. 1 | 2.7:1 |
| Ex. 2 | 1.3:1 |
| Ex. 3 | 1.2:1 |
| Ex. 4 | 1.2:1 |
| Ex. 5 | 0.74:1 |
| Ex. 6 | 0.7:1 |
| Ex. 7 | 1.5:1* |
| Ex. 8 | 1.1:1* |
| Ex. 9 | 1.1:1* |
| Ex. 10 | 1.0:1* |

*The alloy contained two parts by weight of Ag—Cu—Sn powder and one part by weight of Ag—Cu—Pd powder, so that the alloy had an overall composition of 67.2 wt % Ag, 12.0 wt % Cu, 17.4 wt % Sn, and 3.4 wt % Pd.

Tests

Cylindrical-shaped specimens (4 mm in diameter and 8 mm in height) were used for compressive strength and creep tests. The specification of the specimens was complied with ADA Spec. No. 1 for the measurement of mechanical properties of dental amalgams. The compressive strengths of the various amalgams (aged at 37° C. for 1 h and 24 h) were measured using a Shimatzu AGS-500D dynamic mechanical tester (Shimatzu Corp., Kyoto, Japan) at a crosshead speed of 0.5 mm/mm. The creep values of the amalgams were determined at 37° C. under a pressure of 36 MPa for 4 hr. The creep strains were calculated using the equation, Creep= $(L_4-L_1)/L_0 \times 100\%$, where Lo is the original length of the specimens, $L_1$ is the creep strain after 1 hr and $L_4$ is the creep strain after 4 hr. All compressive strength and creep data were averages of ten tests under each condition. One-way ANOVA was used to evaluate the data. In all cases a statistical difference was considered significant at $p<0.05$ level.

Amounts of released mercury vapour were determined by a mercury vapour detector (Jerome 511, Ariz., USA) that used a gold foil sensor as the basis of detection. The (gold foil sensor adsorbed and integrated the mercury vapour, registering a proportional change in resistance. The resulting signal was displayed digitally in the nanogram range. The saturation limit of the gold foil was 1000 ng, while the measurement accuracy was ±5% for 46 ng mercury. The main portion of the reaction apparatus was a cylindrical-shaped glass (4.5 cm diameter), which contained a reaction vessel and a bubbler. The bubbler was connected to a zero air filter for input air. A glass reaction chamber with an inner diameter of 2.0 cm was placed at the center of the reaction vessel. The bottom portion of the reaction chamber had four small openings (1.5 mm in diameter) and was placed right above the detected sample. The bottom opening of the reaction vessel was sealed with a rubber stopper, which contained a mandrel-shaped acrylic sample holder. The center of the mandrel was a cylinder of 1 cm diameter and 2 cm height. The sample was placed at the top of this cylinder. During testing, the mercury vapour evaporating from the specimen surface was drawn through the four small openings at the bottom of the reaction chamber by an internal mechanical pump. Room temperature (25° C.) air with a relative humidity of approximately 50% was pumped through the chamber at a rate of 850 ml/ min, which is equal to the suction rate of the analyzer. The glass cylinder was connected to the analyzer by a Tygon tubing through an external acidic gas filter. During each measurement, the duration of air flow into the analyzer was 30 s. In order to increase the operation hours of the gold sensor, a Dilution Module 10:1 filter (Jerome 511 ) was placed at the end of the Tygon tube. This filter could dilute the mercury vapour concentration to one tenth of its original strength.

At the beginning of each measurement, the gold foil was heated for 1 minute and reheated for 10–15 minutes according to the heating process prescribed by the manufacturer to ensure that there was no mercury left on the gold foil from the previous run. Disc-shaped specimens were used for mercury vapor measurement. After trituration samples were hand condensed into a disc-shaped acrylic die of 1 cm diameter and 2 mm thickness. After condensation the excess mass was removed from the surface, samples then immediately placed at the bottom of the detection chamber. The first reading was taken after 30s. Within the first 30 minutes, readings were taken at 5-min intervals. From 30 to 90 min, readings were taken at 10-mint inervals. From 90 to 180 min, readings were taken at 30-min intervals. After each measurement, the specimen was removed from the detection chamber and clean air was pumped through the analyzer until the reading dropped hack to zero, to ensure that no mercury vapor was left in the chamber.

Results

The results of the above-mentioned tests for samples of Examples 1 to 10 are listed in Table 5.

TABLE 5

|  | Hg:alloy ratio | Compressive strength (MPa) | | Creep (%) | Initial Hg vapor release rate (pg/mm$^2$s)[a] |
|---|---|---|---|---|---|
|  |  | 1 hr | 2 hr |  |  |
| Ex. 1 | 2.7:1 | 52.7 ± 2.06 | 95.1 ± 2.25 | 10.5 ± 2.92 | 141.5 |
| Ex. 2 | 1.3:1 | 83.8 ± 2.81 | 383.0 ± 11.7 | 0.24 ± 0.17 | 30.6 |
| Ex. 3 | 1.2:1 | 100.9 ± 2.51 | 377.6 ± 1.85 | 0.34 ± 0.06 | 42.4 |
| Ex. 4 | 1.2:1 | 106.3 ± 2.65 | 368.8 ± 12.9 | 0.38 ± 0.05 | 32.7 |
| Ex. 5 | 0.74:1 | 241.3 ± 6.03 | 451.7 ± 32.7 | 0.18 ± 0.03 | 54.2 |
| Ex. 6 | 0.7:1 | 171.1 ± 18.8 | 354 ± 39.3 | 0.31 ± 0.07 | 25.9 |
| Ex. 7 | 1.5:1 | 64.6 | 309.4 | 3.88 | 35.3 |
| Ex. 8 | 1.1:1 | 84.6 | 367.5 | 1.76 | 7.1 |

[a] within 1 minute counted from the start of trituration

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

We claim:

1. An amalgamatable dental alloy powder for making an amalgam having a low initial mercury vapor release rate having a composition comprising 50–80 wt % Ag; 10–30 wt % Cu, and 10–35 wt % Sn, and optionally less than 7 wt % of Pd, and having a particle size ranging from 1 to 100 microns with a majority thereof having a particle size less than 45 microns, which is prepared by a process comprising the following steps i) and ii), or steps I), II), and III):

i) subjecting a single-alloy powder having a particle size ranging from 1 to 55 microns with a majority thereof having a particle size less than 20 microns to a heat treatment A; said single-alloy powder comprising 50–80 wt. % Ag, 10–30 wt. % Cu, 10–35 wt. % Sn and optionally less than 7 wt. % Pd;
   ii) subjecting the heat treated single-alloy powder to a pickling treatment;
   I) subjecting a Ag—Cu—Sn powder having a particle size ranging from 1 to 70 microns with a majority thereof having a particle size less than 30 microns to a heat treatment B, and subjecting a Ag—Cu—Pd powder having a particle size ranging from 1 to 100 microns with a majority thereof having a particle size less than 45 microns to a heat treatment C;
   II) subjecting the heat treated Ag—Cu—Sn powder and the heat treated Ag—Cu—Pd powder to a pickling treatment; and
   III) mixing the resulting Ag—Cu—Sn powder and the resulting Ag—Cu—Pd powder obtained from step II) to form an amalgamatable dental alloy having a composition comprising 50–80 wt. % Ag, 10–30 wt. % Cu, 10–35 wt. % Sn and optionally less than 7 wt. % Pd;
   wherein said heat treatments A, B and C independently comprise heating said powder at a temperature ranging from 100 to 600° C. in an inert atmosphere for a period ranging from 0.5 hours to 8 days, provided that said powder remains in a powder form or in a loose agglomerate form after said heat treatment.

2. The amalgamatable dental alloy powder according to claim 1, wherein said heat treatments A, B and C independently comprise heating said powder at a temperature ranging from 100 to 500° C. and for a period ranging from 24 hours to 48 hours.

3. The amalgamatable dental alloy powder according to claim 1, wherein said composition is free from Pd and said alloy powder is prepared by the process comprising steps i) and ii).

4. The amalgamatable dental alloy powder according to claim 1, wherein said composition comprises Pd and said alloy powder is prepared by the process comprising steps i) and ii).

5. The amalgamatable dental alloy powder according to claim 3, wherein said heat treatment A comprises heating said single-alloy powder at a temperature ranging 300 to 500° C. and for a period ranging from 24 hours to 48 hours.

6. The amalgamatable dental alloy powder according to claim 4, wherein said heat treatment A comprises heating said single-alloy powder at a temperature ranging 300 to 500° C. and for a period ranging from 24 hours to 48 hours.

7. The amalgamatable dental alloy powder according to claim 5, wherein said composition comprises 60–70wt % Ag; 10–20 wt % Cu, and 10–30wt % Sn.

8. The amalgamatable dental alloy powder according to claim 7, wherein said composition comprises 60 wt % Ag, 13 wt % Cu and 27 wt % Sn.

9. The amalgamatable dental alloy powder according to claim 6, wherein said composition comprises 10–20 wt % Sn.

10. The amalgamatable dental alloy powder according to claim 9, wherein said composition comprises 60–70 wt % Ag; 10–20 wt % Cu, and 2–4 wt % Pd.

11. The amalgamatable dental alloy powder according to claim 1, wherein said alloy powder is prepared by the process comprising steps I), II) and III).

12. The amalgamatable dental alloy powder according to claim 11, wherein a majority of the particles of said Ag—Cu—Sn powder have a particle size less than 20 microns and a majority of the particles of said Ag—Cu—Pd powder have a particle size less than 35 microns.

13. The amalgamatable dental alloy powder according to claim 12, wherein a majority of the particles of said Ag—Cu—Sn powder have a particle size less than 10 microns and a majority of the particles of said Ag—Cu—Pd powder have a particle size less than 25 microns.

14. The amalgamatable dental alloy powder according to claim 11, wherein said heat treated Ag—Cu—Sn powder and said heat treated Ag—Cu—Pd powder are separately subjected to said pickling treatment.

15. The amalgamatable dental alloy powder according to claim 11, wherein said heat treatment B comprises heating said Ag—Cu—Sn powder at a temperature ranging from 300 to 500° C. for a period ranging from 24 hours to 48 hours, and said heat treatment C comprises heating Ag—Cu—Pd powder at a temperature ranging from 100 to 500° C. for a period ranging from 24 hours to 48 hours.

16. The amalgamatable dental alloy powder according to claim 15, wherein said heat treatment B comprises heating said Ag—Cu—Sn powder at 400° C. for 24 hours, and said heat treatment C comprises heating Ag—Cu—Pd powder at a temperature ranging from 100 to 400° C. for 48 hours.

17. The amalgamatable dental alloy powder according to claim 15, wherein said composition comprises 60–70 wt % Ag; 10–20 wt % Cu, 10–30 wt % Sn and 2–4 wt % Pd.

18. The amalgamatable dental alloy powder according to claim 16, wherein said composition comprises 60–70 wt % Ag; 10–20 wt % Cu, 10–30 wt % Sn and 2–4 wt % Pd.

19. The amalgamatable dental alloy powder according to claim 17, wherein said composition comprises 67.2 wt % Ag, 12.0 wt % Cu, 17.4 wt % Sn, and 3.4 wt % Pd.

20. The amalgamatable dental alloy powder according to claim 18, wherein said composition comprises 67.2 wt % Ag, 12.0 wt % Cu, 17.4 wt % Sn, and 3.4 wt % Pd.

21. The amalgamatable dental alloy powder according to claim 19, wherein said Ag—Cu—Sn powder comprises 70 wt % Ag, 4 wt % Cu and 26 wt % Sn, and said Ag—Cu—Pd powder comprises 62 wt % Ag, 28 wt % Cu and 10 wt % Pd.

22. The amalgamatable dental alloy powder according to claim 20, wherein said Ag—Cu—Sn powder comprises 70 wt % Ag, 4 wt % Cu and 26 wt % Sn, and said Ag—Cu—Pd powder comprises 62 wt % Ag, 28 wt % Cu and 10 wt % Pd.

* * * * *